United States Patent
Tokoyama

Patent Number: 5,309,773
Date of Patent: May 10, 1994

[54] POWDER AND GRANULE INSPECTION APPARATUS

[75] Inventor: Katsumi Tokoyama, Osaka, Japan

[73] Assignee: Hajime Industries Ltd., Tokyo, Japan

[21] Appl. No.: 753,064

[22] Filed: Aug. 30, 1991

[30] Foreign Application Priority Data

Sep. 13, 1990 [JP] Japan ............... 2-97154[U]

[51] Int. Cl.$^5$ .................. G01N 1/12; G01N 1/34; G01N 21/85

[52] U.S. Cl. .................. 73/863.01; 73/863.02; 73/863.54; 73/863.58; 73/863.81; 250/576; 250/222.2; 250/223 R; 356/426; 209/576

[58] Field of Search ............ 73/863.01, 863.02, 863.03, 73/863, 863.21, 863.54, 863.52, 863.58, 863.81, 863.83, 864.73, 864.74, 866; 356/426; 250/576, 577, 222.2, 223 R, 431; 209/576, 910, 643; 198/341; 141/83, 95, 198, 324, 331; 406/32, 33, 34, 52

[56] References Cited

U.S. PATENT DOCUMENTS

| | | | |
|---|---|---|---|
| 797,144 | 8/1905 | Nickerson | 73/863.52 X |
| 850,293 | 4/1907 | Calkins | 73/863.52 X |
| 2,020,281 | 11/1935 | Stone et al. | 356/426 X |
| 2,701,055 | 2/1955 | Strom, Jr. | 356/426 X |
| 2,790,548 | 4/1957 | Scherer | 209/910 X |
| 3,561,273 | 2/1971 | Tanila | 73/863.01 |
| 4,120,203 | 10/1978 | Clements et al. | 73/863.57 X |
| 4,572,666 | 2/1986 | Satake | 209/588 X |
| 4,718,288 | 1/1988 | Leschonski et al. | 73/863 |
| 4,756,348 | 7/1988 | Moller | 222/55 X |
| 5,135,114 | 8/1992 | Satake et al. | 209/643 X |
| 5,242,059 | 9/1993 | Low et al. | 209/643 X |

FOREIGN PATENT DOCUMENTS

| | | | |
|---|---|---|---|
| 364786 | 4/1990 | European Pat. Off. | 209/576 |
| 3427535 | 2/1986 | Fed. Rep. of Germany | 209/576 |
| 60519 | 3/1989 | Japan . | |
| 249904 | 10/1990 | Japan | 356/426 |
| 364877 | 12/1972 | U.S.S.R. | 250/222.2 |
| 325376 | 2/1930 | United Kingdom | 73/863.02 |

*Primary Examiner*—Tom Noland
*Attorney, Agent, or Firm*—Bauer & Schaffer

[57] ABSTRACT

A sample of powder granules flowing through an online conveyor is removed periodically and fed to a supply hopper where a predetermined amount of granules are stored. A small portion of the granules are removed from the supply hopper and continuously fed to the upper surface of a rotary table to form a single layer thereon. The sample on the table is optically sensed to detect foreign particles. The foreign particles are removed and subsequently the good particles are removed and passed to a weighing hopper. The ratio of good product after sensing and the sample in the hopper is calculated to determine the relative amount of foreign particles flowing in the system.

6 Claims, 6 Drawing Sheets

POWDER AND GRANULE INSPECTION APPARATUS

BACKGROUND OF THE INVENTION

1. Field of the Invention

The present invention relates to apparatus for inspecting powder granules and more particularly to a powder granule inspection apparatus that samples powder granules (such as powders, pellets, granules and so on) that flow through an online conveyor tube so as to automatically conduct inspection for foreign particles contained therein and to remove the foreign particles, and that is arranged to shorten the time from the sampling of powder granules to the inspection thereof as much as possible so that the inspection results become available within a short period of time.

2. Description of the Prior Art

In a known apparatus, a certain amount of the sampled powder granules is accumulated in a hopper, from which a small amount of the powder granules is removed and supplied to the top of a rotating table. The moving powder granules are picked up by a photosensing device and the size and number of foreign particles therein are detected. The ratio of the foreign particles relative to the amount of powder or granule in the hopper is then determined relative to a predetermined standard. In this case, the certain amount of powder granules was set at relatively large amount (such as about 500 grams).

However, this prior art apparatus does not conduct the inspection during the time that the certain amount of powder granules is being accumulated in the hopper. Therefore a long period of time is required from the time inspection is initiated until it is completed. This causes a delay in the availability of the inspection result so that when powder granules flowing through an online conveyor contain excessive amount of foreign particles it will only be possible to detect the foreign particles after a large amount of such powder granules have entered the production line and their removal would be inconvenient.

OBJECTS AND SUMMARY OF THE INVENTION

Accordingly, it is an object of the present invention to provide a powder granule inspection apparatus which provides the inspection result within a short period of time by shortening the time from the start of sampling to its actual inspection.

According to the present invention, there is provided a powder granule inspection apparatus that samples powder granules flowing through an online conveyor tube by pneumatically withdrawing a sampling of the powder granules, automatically inspecting for foreign particles contained in the sampled powder granules and removing much foreign particles if any, which comprises:

a) a supply hopper for continuously sorting a predetermined amount of the powder granules;

b) a feeder for cutting out from the supply hopper a small amount of powder granules and continuously feeding the cutout powder granules onto the surface of a rotary table in the form of a single layer;

c) a photosensing device for picking up and detecting any foreign particles contained in the powder granules on the rotary table surface;

d) a foreign particle remover for removing the foreign particle from the rotary table;

e) a good product remover for removing the powder granules from which the foreign particle has been removed from the rotary table;

f) a weighing hopper for temporarily storing a predetermined amount of good powder granules that have been removed from the rotary table by the product remover; and g) means for maintaining the predetermined amount of powder granules in the supply hopper such that the predetermined amount of powered granules is slightly larger than the amount of powered granules being cut out by the feeder device, and the amount of powder granules diverted from the online conveyor tube is larger than the cutout amount of powder granules by said feeder device.

A better understanding of the objects, features and advantages of the invention will be gained from a consideration of the following detailed description of the preferred embodiments thereof, in conjunction with the figures of the accompanying drawings through which like references designate same and similar elements.

DETAILED DESCRIPTION OF THE PREFERRED EMBODIMENT

An embodiment of the powder granule inspection apparatus according to the present invention will now be described with reference to the drawings.

Figure 1:
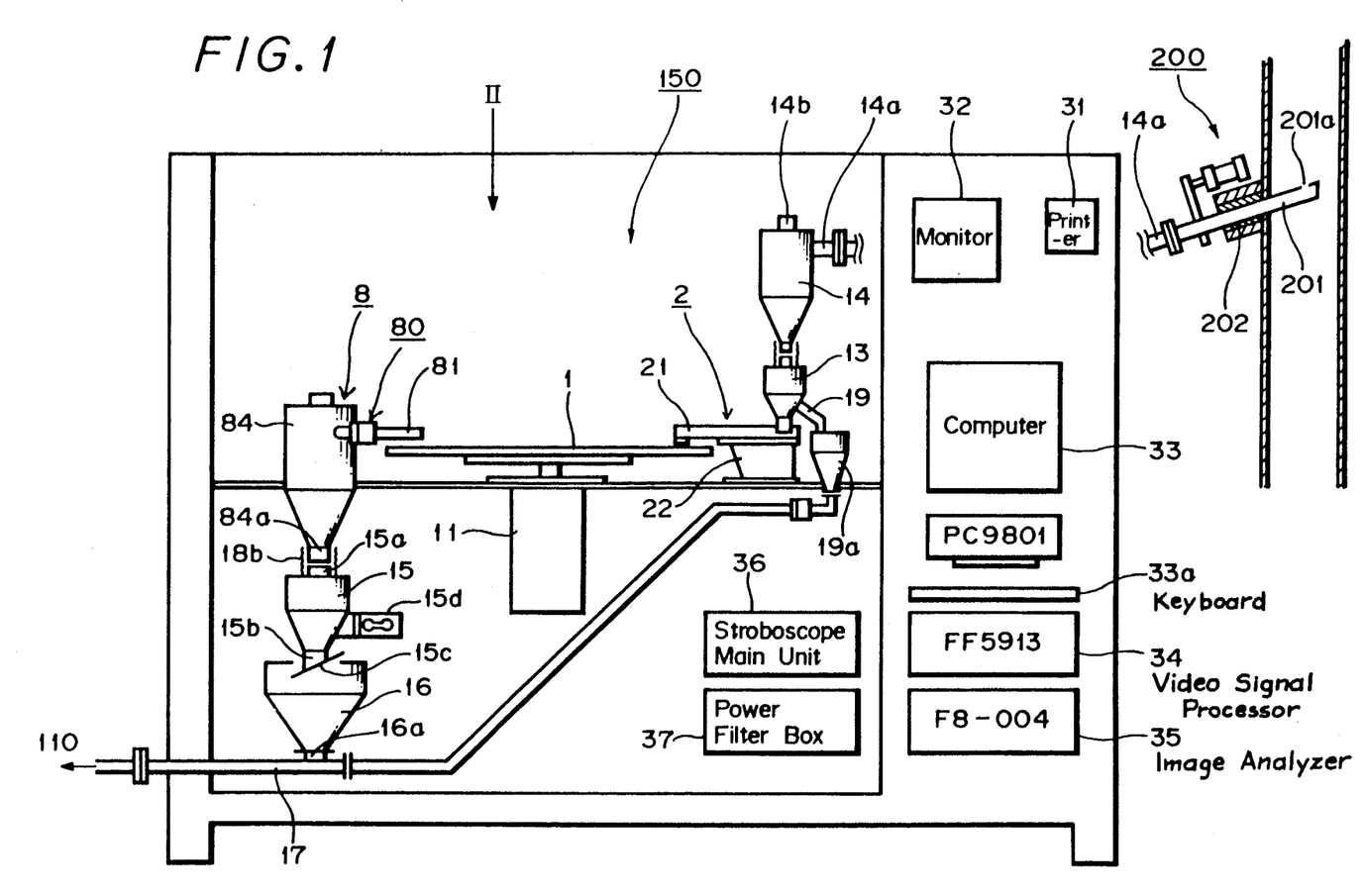
FIG. 1 is a partial sectional side view of an embodiment of the powder granule inspection apparatus according to the present invention.
Figure 2:
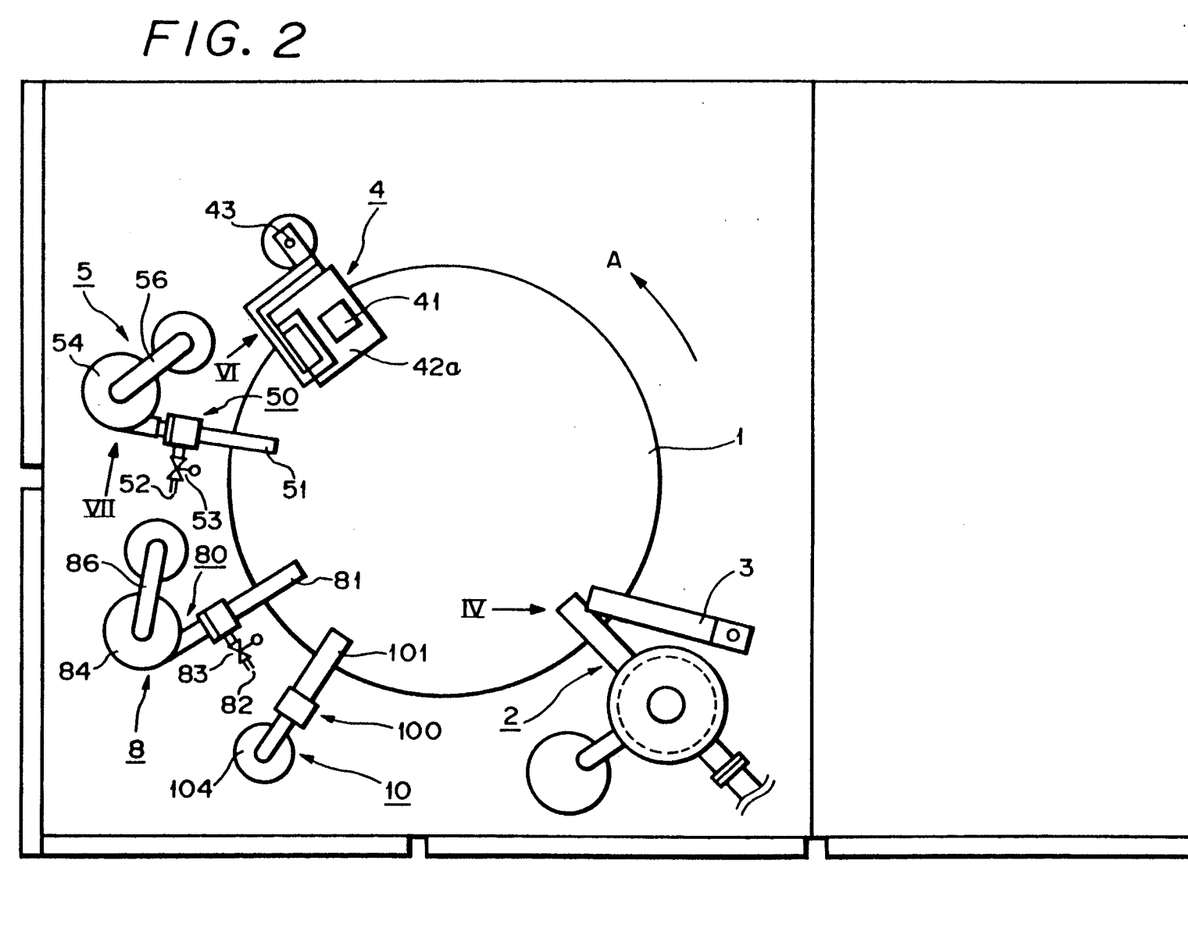
FIG. 2 is a plan view of FIG. 1 seen from an arrow II.

In FIG. 1 and 2 a powder granule inspection apparatus according to the present invention is provided with an online tube 110 for pneumatically transferring huge amounts of powders (pellets) from a supply to a production line, etc. In this apparatus samples of the powder granules that flow through the online conveyor tube 110 are diverted by a sampling nozzle 200 and fed to the detecting apparatus generally depicted by the numeral 150 where the size and number of foreign particles contained in the powder granules are determined.

The detection apparatus 150 comprises a rotary table 1, about the circumference of which there are placed in sequence, a feeder device 2 which continuously feeds the powder granules in a line and at a single layer on the surface of the rotary table 1, a static electricity remover 3 that removes the static electricity from the powder granules on the surface of the rotary table 1, a foreign particle inspection device 4 that photosenses, from above the table, the powder granules on the rotary table 1 to determine the size and number of the foreign particles contained in the powder granules. In addition a foreign particle remover 5 removes by suction the foreign particles that were detected by the foreign particle inspection device 4, and a good product remover 8 removes by suction the good powder granules after the foreign particles have been removed. Lastly, a cleaner 10 vacuums the small residue of the powder granules that have remained on the surface of rotary table 1.

As shown in FIG. 1, a supply hopper 13 and a cyclone 14 are placed above the feeder device 2 and a metering or weighing hopper 15 and a receiving hopper 16 are placed beneath the good product remover 8. The outlet mouth 16a at the bottom of the receiving hopper 16 is connected to a good product recovery transfer tube 17.

Figure 3:
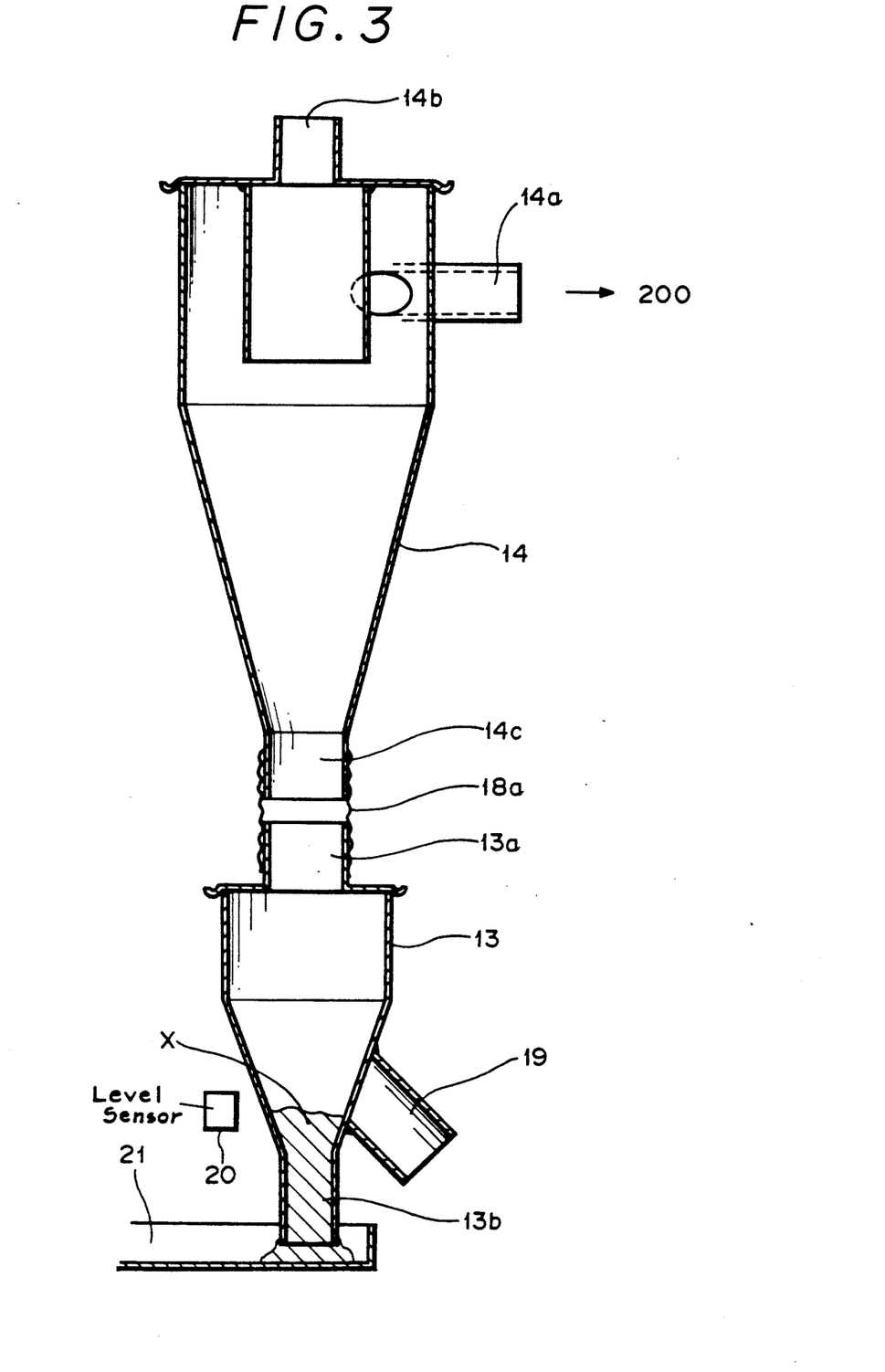
FIG. 3 is an enlarged sectional view of the supply hopper and a cyclone shown in FIG. 1.

The cyclone 14 as seen in enlargement in FIG. 3 is connected to the sampling nozzle 200 via sample transfer tube 14a and has an air exhaust tube extending upward at its top. At the bottom of the cyclone an outlet mouth 14c is connected to an intake mouth 13a leading to the supply hopper 13 via a bellows 18a. The supply hopper 13 has an overflow tube 19 which also communicates with the good product recovery transfer tube 17 via an intermediate hopper 19a, as shown in FIG. 1.

The rotary table 1 is made of, for example, colourless transparent glass plate and its surface is generally flat. A rotary drive mechanism 11 placed under the rotary table 1 comprises a motor having a rotary shaft extending perpendicularly upward connected to the center of the rotary table 1. The motor rotates the rotary shaft and thus the the table at a preset speed.

Figure 4:
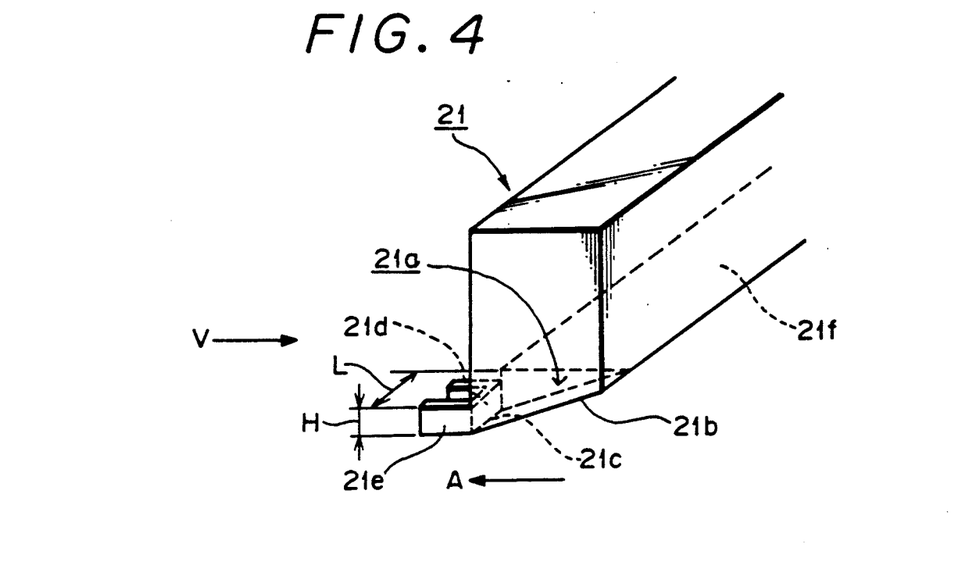
FIG. 4 is an enlarged view of the feeder as seen from an arrow IV in FIG. 2.
Figure 5:
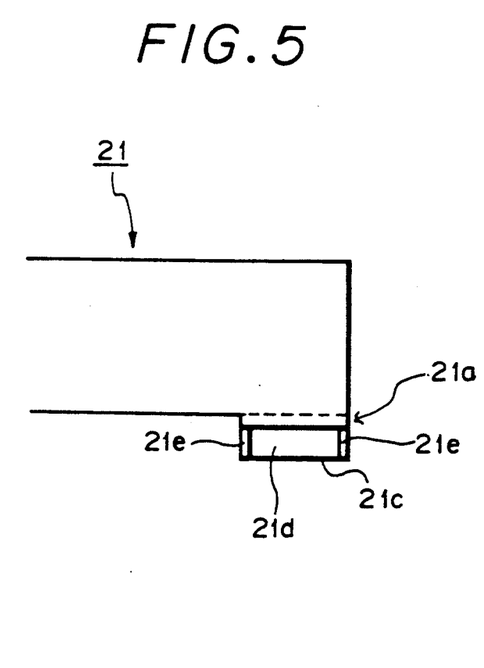
FIG. 5 is a side view of the feeder as seen from an arrow V in FIG. 4.

The feeder device 2 as seen in detail in FIGS. 4 and 5 comprises a tubular body or trough 21 having a square cross section. An electromagnetic coil 22 is placed beneath the trough 21 to provide vibration to the trough 21. The supply hopper 13 is placed at one end of the trough so that its bottom outlet mouth 13b is inside the trough 21, passing through an opening formed on the top surface of trough 21. The other outlet end of trough 21 is placed above the rotary table 1 in a manner as shown on FIG. 4.

The outlet end of trough 21 in its lengthwise direction is closed and a laterally protruding tubular section 21a having lengthwise direction L is formed. The protruding tubular section 21a has an inclined bottom plate 21b that is tilted towards the rotation direction A of the rotary table 1 and its lower edge 21c is placed above the top surface of the rotary table 1, at a distance that is smaller than the grain diameter of the powder granules. An opening 21d having height H is provided in inside wall of the trough and small wall pieces 21e are placed either side of the opening 21d to protrude in the rotation direction. It is to be noted that the length L is selected to be slightly larger than twice the diameter of the powder granule grain while the dimension H is set to be slightly larger than the grain diameter. Thus, when the powder granules slide down on the surface of bottom plate 21b the grains will not pile up in layers on passing the opening 21d and further will appear in aligned status of 2 rows contained within the protruding pieces 21e. Further, the vibration effected on the trough 21, by the electromagnetic coil 22, is so selected that the powder granules moving along the bottom wall of 21f of the trough will positively assume a single layer. The bottom wall 21f and the bottom wall 21b of the outlet can also be arranged so that there will be no step difference between them but rather be a continuous slanted surface.

Figure 6:
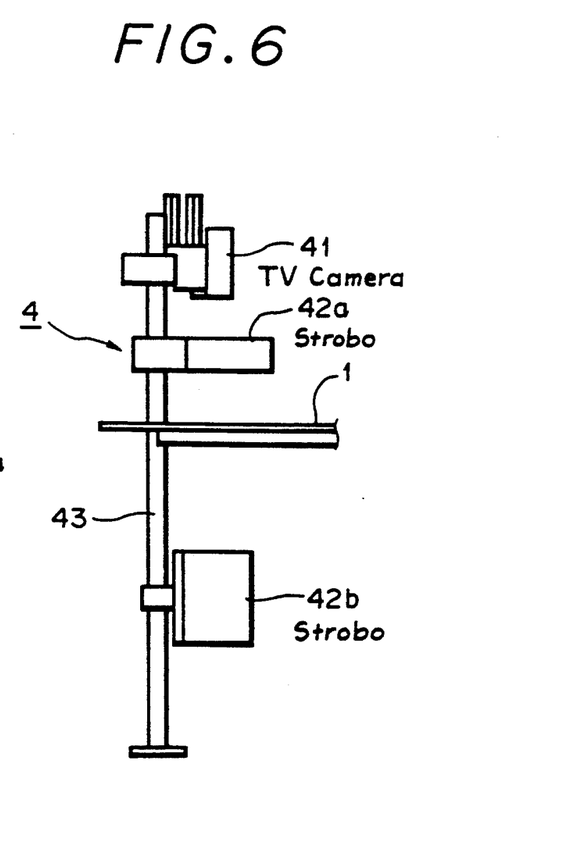
FIG. 6 is a side view of the inspection device as seen from an arrow VI in FIG. 2.

In FIG. 6 the foreign particle inspection device 4 is shown. This foreign particle inspection device 4 has a television camera (CCD) 41 and two stroboscope lights 42a, 42b. Stroboscope 42a is placed above the rotary table 1 along with the television camera 41, while the stroboscope 42b is place beneath the rotary table 1 in opposition to the stroboscope 42a. A support stand 43 is provided for supporting the television camera 41, and stroboscopes 42a, 42b and to provide adjustment.

Figure 7:
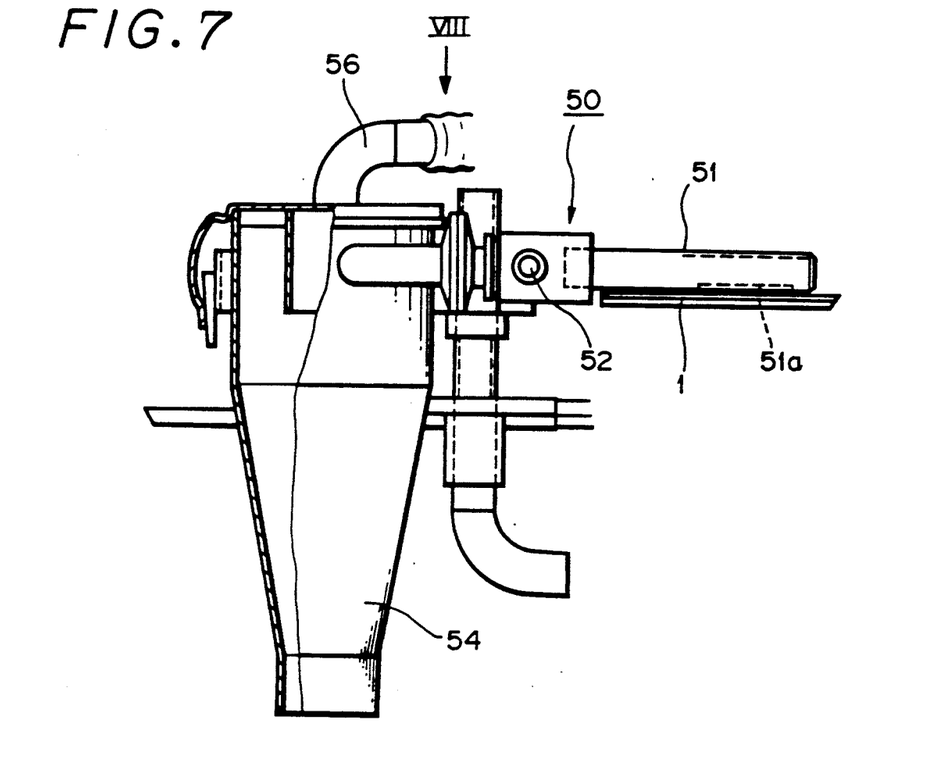
FIG. 7 is a side view of the good product remover as seen from an arrow VIII in FIG. 2.
Figure 8:
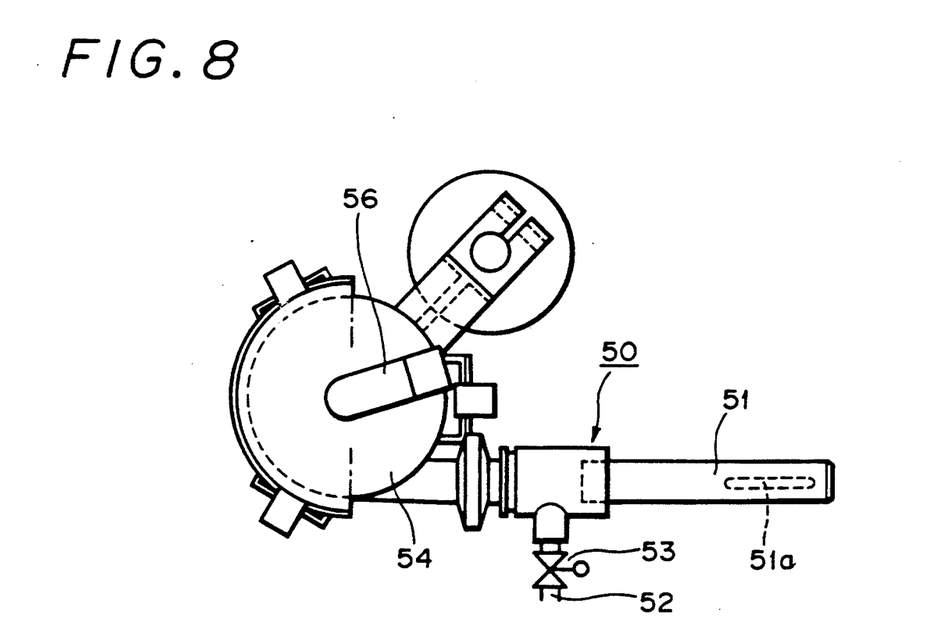
FIG. 8 is a side elevational view of the good product remover as seen from an arrow VIII of FIG. 7.

The foreign particle remover 5 is shown in FIGS. 7 and 8, comprising a suction ejector, comprising a suction pipe 51, an air supply tube 52 and valve 53. The suction pipe 51 is connected at one end to cyclone 54 and is provided with a long slender suction mouth 51a at the other end which is placed close and parallel to the surface of the rotary table 1 so that any foreign particle contained in the powder granules on the rotary table 1 can be positively absorbed.

The air supply tube 52 is connected to an air compressor (not shown) at its free end, while its other end is connected to suction pipe 51 in a manner to supply air to the ejector in a countering direction to that of the suction mouth 51a. Valve 53 adjusts the airflow within air supply tube 52. An air outflow hose 56 at the top of cyclone 54, is connected to a dust collector (not shown.)

The good product remover 8 is of the same structure as the foreign particle remover 5, and contains as shown in FIG. 2, a suction ejector 80 (suction pipe 81, air supply tube 82 and valve 83), a cyclone 84 and air outflow hose 86. The cleaner 10 is also formed of, as shown on FIG. 2 with the same structure as foreign particle remover 5 and good product remover 8, that is with a suction ejector 100 (suction pipe 101, etc.) and cyclone 104 etc. Foreign particle remover 5 is arranged in association with and in response to the foreign particle inspection device 4 and rotary drive mechanism 11 so that detected foreign particles will be absorbed by suction mouth 51a when they arrived directly beneath the suction mouth 51a of the suction ejector 50.

In FIG. 1, the bottom outlet mouth 84a of cyclone 84 in the good product remover 8, is connected to the upper inlet mouth 15a of the weighing hopper 15 via bellows 18b. A bottom outlet mouth 15b of the weighing hopper is generally left freely opening or selectively closed by cover 15c. A load cell 15d is installed at the side of the weighing hopper 15 and is arranged to weigh the powder granules (good product) accumulated within weighing hopper 15 upon closing the cover 15c. The bottom outlet mouth 15b of the hopper 15 is located inside the receiving hopper 16.

As seen in FIG. 3, the overflow tube 19 is connected to the supply hopper 13 at its somewhat upper portion from the bottom outlet mouth 13b and is oriented in a slanted downward direction, so that the powder granules in the cyclone 14 over the level indicated by X in FIG. 3, will flow into overflow tube 19, and thereby a fixed amount of powder granules (below the level X) will be constantly maintained in the hopper 13. It is preferably arranged so that the amount of powder granules X will be slightly larger than the amount of powder granules cut out by the feeder device 2 while the sampled amount of powder granules diverted from the online conveyor tube by the sampling nozzle 200 will be greater than the amount of powder granules cut out by the feeder device 2.

The supply hopper 13 is also provided with a sensor 20 that detects the upper and lower limits of the powder granule amounts accumulated therein. When the powder granules accumulated amount in hopper 13 reaches an upper limit, the sensor outputs a signal to move the sampling nozzle 200 to a position where it will not divert powder granules. When the powder granule accumulated amount is sensed to be less than a predefined lower limit, the sensor outputs an abnormal signal.

Figure 9:
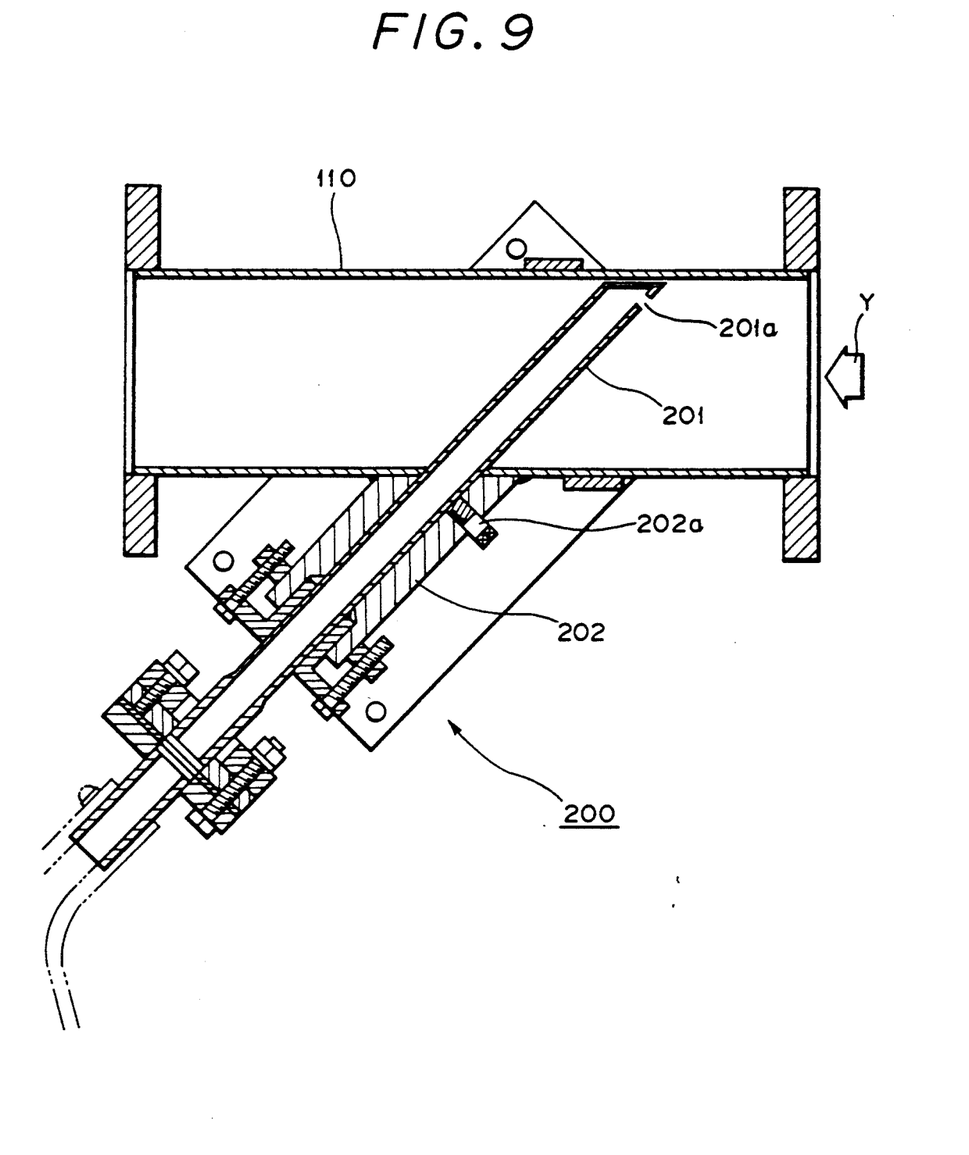
FIG. 9 is an enlarged, sectional view of a sampling nozzle.

FIG. 9 shows an enlarged cross section diagram of sampling nozzle 200. Sampling nozzle 200 is so arranged that its sampling tube 201 is freely slidable into the online tube 110 through sleeve 202. The sampling tube 201 has its forward tip end closed and is formed with a sampling hole 201a through its side wall. The sampling hole 201a is arranged to face upstream of the online tube 110; the powder granule flow direction inside the online tube 110 being shown by the arrow Y. Through the side wall of sleeve 202, air blow-in mouth 202a is provided that connects with sampling hole 201a when the tip end of sampling tube 201 is inserted into the wall of the online tube 110.

Turning back to FIG. 1, the system includes a printer 31, prints out the inspection data; a monitor 32 on which the image from television camera 41 is displayed; a computer 33 (such as model PC9801 video processor, which is manufactured by NED Corp.) that controls the function of the entire device as well as memorizes the inspection data, and its keyboard 33a; an FF5913 video signal processor 34, which is manufactured by Hajime Industries Ltd.; and an F8-004 image analyzer 35, which is manufactured by Hajime Industries Ltd. and provided to determine the existence of foreign particles within the powder granules by image analysis of the video signals from television camera 41. A stroboscope control unit 36 which regulates the cycle, etc. of stroboscopes 42a, 42b, and a power filter box 37 that controls the power source for the apparatus is also provided.

The operation of the above embodiment will be explained. Firstly, the sampling tube 201 of the sampling nozzle 200 is set at the specified position in the online tube 110. The powder granules diverted through sampling hole 201a is transferred to cyclone 14 through the transfer tube 14a and are separated within the air in cyclone 14. The air escapes out through air outlet pipe 14b while the powder granules drop down inside the supply hopper 13 and accumulate inside supply hopper 13 after being blocked by the trough 21. After a specified amount X (such as 40 grams) of the sampled powder granules is accumulated as shown in FIG. 3, the feeder device 2 is activated and the powder granules inside supply hopper 13 are removed at a predetermined rate by vibrating the trough 21 by operating the electromagnetic coil 22. The granules are gradually transferred within the trough 21 towards the rotary table 1 in an aligned condition in a uniform direction.

Since the amount of powder granules diverted by the nozzle 200 is arranged to be slightly greater than the amount removed by feeder device 2, an amount of powder granules that exceeds the X amount is sent to hopper 13. However, such excessive powder granules flow into the overflow tube 19 and are discharged so that they do not accumulate within supply hopper 13. Thus, the X amount is steadily maintained. Also since the X amount is arranged to be slightly in excess of the amount removed by the feeder device 2, the accumulated powder granule inside supply hopper 13 will promptly be removed and and sent to the rotary table 1 by the feeder 2.

The powder granules that are loaded on the rotary table 1 are transferred at a predetermined speed in the direction of arrow A (FIG. 2), being driven by the rotary drive mechanism 11. When the powder granules on the rotary table 1 pass beneath the television camera 41 at the foreign particle inspection device 4, it is optically viewed, at which time the powder granules are intermittently irradiated by stroboscopes 42a, 42b in order to detect foreign particles. Since the powder granules are irradiated from both of the front and back sides of the rotary table 1, there will be no occurrence of shadows created by the stroboscope lights on the surface of the rotary table 1 eliminating any chance of misdetected foreign particles.

Then, the foreign particles within the sample are sucked out by the ejector 50. Since the rotary table 1 is hard, there is no fear that it will warp to cause suction mouth 51 to become clogged. Also, since the surface of the rotary table 1 is flat and the suction mouth 51a is arranged to be in parallel to its surface, the suction power from ejector 50 will be applied evenly across the surface of the table so that the suction power will effect all of the foreign particles that are under the suction mouth 51a. The vacuumed foreign particles are discharged to a container (not shown) that is placed under cyclone 54.

Thereafter the good product or the powder granule from which the foreign particles have been removed is vacuumed from the rotary table 1 surface by the good product remover 8. The good product is separated with air in the cyclone 84, dropped down and sent through weighing hopper 15, the receiving hopper 16 when cover 15c is opened, to the good product recovery transfer tube 17. Simultaneously the powder granules that flow into overflow tube 19 from the supply hopper 13 is also sent to the good product recovery transfer tube 17 via hopper 19a. The residual powder granules that were not removed, even when passing under good product remover 8, are vacuumed from the rotary table 1 surface by subsequently passing cleaner 10.

In order to obtain the ratio of foreign particles relative to the sample powder granules the cover 15c is closed for a certain time period T. Measurement is made of the amount of powder granules accumulated in the weighing hopper 15 during such time period T. At the same time the number and sizes of foreign particles that have been detected by the foreign particle inspection device 4 during such time period T are calculated. The ratio thus obtained is converted to a value corresponding to a given powder granule amount (for example 50 grams), so that the accumulated amount of powder granule in the weighting hopper 15 may be relatively small.

According to the above described inspection apparatus of the present invention, the powder granules diverted from the online tube 110, is sent to the rotary table 1 and is inspected in a very short time as compared to the conventional systems. Further, the foreign particle ratio relative to the powder granule can be made available by only using a small amount of the powder granule. Therefore, the inspection results on the sample powder granule can be obtained within an extremely short time and in extremely short intervals.

According to the powder granule inspection apparatus of the invention as above described, since only a slightly greater amount of the powder granule than the amount removed by feeder device 2 accumulates in the supply hopper 13 by reason of connection of the overflow tube 19 thereto, the powder granule from online conveyor tube 110 can be sent to the rotary table 1 and inspected within an extremely short period of time. Moreover, since the weighing hopper 15 that temporarily accumulates a randomly set amount of good product only is installed under the good product remover 8, it is possible to obtain the foreign particle ratio by accumulating only a relatively small amount of good powder granule product in the weighing hopper 15. Accordingly, the inspection results of the sample powder granule can be obtained within an extremely short period of time.

In another embodiment of the present invention, a foreign particle inspection device that optically views the powder granule from the surface of the rotary table 1 from beneath the table may be used. In addition, foreign particle remover may be arranged to remove such detected foreign particles. According to this arrangement, foreign particles that only can be seen from beneath the rotary table 1 can also be detected and removed, so that the reliability of the test results may be improved.

Further, a static electricity remover may be installed before the cleaner 10 to remove any charge from the residue.

It should be understood that the above description is presented by way of example of the preferred embodiment of the invention and it will be apparent that many modifications and variations thereof could be effected by one with ordinary skill in the art without departing from the spirit and scope of the novel concepts of the invention so that the scope of the invention should be determined only by the appended claims.

I claim as my invention:

1. A powder granule inspection apparatus for sampling powder granules flowing through an online tube having means for removing a sample of said powder granules by a sampling nozzle, means for automatically inspecting for foreign particles contained in said sampled powder granules and means for removing such foreign particles, if any, comprising:

a) a supply hopper for continuously storing at least a predetermined amount of powder granules sampled by said sampling nozzle;
   b) a feeder device for cutting out a small amount of powder granules from said supply hopper and continuously feeding the cut-out powder granules onto an upper surface of a the rotary table in the form of a single layer;
   c) a photosensing device for optically viewing and detecting the foreign particles contained in said sampled powder granules that are loaded onto the rotary table surface;
   d) a foreign particle remover for removing the foreign particles from the rotary table surface;
   e) a good product remover for removing the powder granules from which the foreign particle has been removed from the rotary table surface;
   f) a weighing hopper for temporarily storing a desired amount of the powder granules that have been removed by said good product remover; and
   g) means for maintaining said predetermined amount of powder granules in said supply hopper such that said predetermined amount of powder granules in said supply hopper is selected to be slightly larger than the amount of powder granules cutout by said feeder device, and the sampled amount of powder granules removed by said sampling nozzle is selected to be larger than the amount of powder granules cutout by said feeder device.

2. A powder granule inspection apparatus as claimed in claim 1, wherein the maintaining means is an overflow tube connected to said supply hopper at a predetermined position so as to drain out powder granules exceeding said predetermined amount from said supply hopper.

3. A powder granule inspection apparatus as claimed in claim 2, wherein an outlet of said overflow tube and an outlet of said weighing hopper are connected to said online tube.

4. A powder granule inspection apparatus according to claim 1 further comprising a weighing hopper with a lid at an outlet end thereof and connected to an outlet opening of said good product remover, and a load cell provided in connection with said weighing hopper to measuring the weight of said good product accumulated in said weighing hopper when said lid is closed.

5. A powder granule inspection apparatus according to claim 4 further comprising a sensor in association with said supply hopper so as to detect an upper and lower limit of the amount of said powder granules accumulated in said supply hopper.

6. A powder granule inspection apparatus as claimed in claim 5, wherein said sensor delivers a signal to said sampling nozzle to move the same to a position where said sampling nozzle does not sample powder granules any more when said sensor detects the upper limit, while said sensor delivers an obnormal signal in a little while after said sensor detects that powder granules become less than the lower limit.

* * * * *